(12) United States Patent
Zhang et al.

(10) Patent No.: US 10,952,429 B2
(45) Date of Patent: Mar. 23, 2021

(54) CORNEAL PRESERVATION AND REHYDRATION DEVICE

(71) Applicant: SHENZHEN AINEAR CORNEA ENGINEERING CO., LTD., Shenzhen (CN)

(72) Inventors: Jinnan Zhang, Shenzhen (CN); Yongmei Yu, Shenzhen (CN)

(73) Assignee: SHENZHEN AINEAR CORNEA ENGINEERING CO., LTD., Shenzhen (CN)

( * ) Notice: Subject to any disclaimer, the term of this patent is extended or adjusted under 35 U.S.C. 154(b) by 476 days.

(21) Appl. No.: 15/745,123

(22) PCT Filed: Jul. 29, 2016

(86) PCT No.: PCT/CN2016/092432
§ 371 (c)(1),
(2) Date: Jan. 15, 2018

(87) PCT Pub. No.: WO2017/020795
PCT Pub. Date: Feb. 9, 2017

(65) Prior Publication Data
US 2018/0206482 A1    Jul. 26, 2018

(30) Foreign Application Priority Data
Jul. 31, 2015 (CN) .......................... 201510466857.7

(51) Int. Cl.
*A01N 1/02* (2006.01)
*A61F 2/00* (2006.01)

(52) U.S. Cl.
CPC .......... *A01N 1/0273* (2013.01); *A01N 1/0263* (2013.01); *A61F 2/0095* (2013.01)

(58) Field of Classification Search
CPC ...... A01N 1/0263; A01N 1/0273; A01N 1/02; A61F 2/0095
See application file for complete search history.

(56) References Cited

U.S. PATENT DOCUMENTS

| 2,929,603 A | 3/1960 | Stewart |
| 5,019,084 A | 5/1991 | Aysta et al. |

(Continued)

FOREIGN PATENT DOCUMENTS

| CN | 201243575 Y | 5/2009 |
| CN | 202558868 U | 11/2012 |

(Continued)

OTHER PUBLICATIONS

International Search Report for PCT/CN2016/092432, dated Jul. 29, 2016, and its English translation provided by WIPO.

(Continued)

*Primary Examiner* — Liban M Hassan
(74) *Attorney, Agent, or Firm* — Ladas & Parry, LLP

(57) ABSTRACT

A corneal preservation and rehydration device includes a box body and a box lid (1), wherein the box body and the box lid are detachably connected. A corneal bracket (2) is provided in the box body for holding a cornea, wherein a surface of the corneal bracket for placing a cornea is a convex spherical surface (21), and a blocking portion (22) is arranged at the surrounding of the convex spherical surface (21) for preventing a cornea from dropping out.

9 Claims, 4 Drawing Sheets

(56) References Cited

U.S. PATENT DOCUMENTS

| | | | | |
|---|---|---|---|---|
| 5,681,740 A | * | 10/1997 | Messier | A01N 1/02 206/438 |
| 2008/0294149 A1 | * | 11/2008 | Krolman | A01N 1/02 606/1 |
| 2011/0008877 A1 | | 1/2011 | Skelnik et al. | |
| 2011/0281352 A1 | | 11/2011 | Raeder et al. | |

FOREIGN PATENT DOCUMENTS

| | | |
|---|---|---|
| CN | 202670278 U | 1/2013 |
| CN | 303499695 S | 12/2015 |
| EP | 0262766 A1 | 4/1988 |
| EP | 2150103 A2 | 2/2010 |
| JP | 07109201 A | 4/1995 |
| SU | 1159534 A1 | 6/1985 |

OTHER PUBLICATIONS

Written Opinion of the International Search Authority for PCT/CN2016/092432, dated Jul. 29, 2016, and its English translation provided by WIPO.
From CN201510466857.7, $1^{st}$ office action, dated Sep. 26, 2016, with an English Translation from Espacenet Global Dossier.
From CN201510466857.7, $2^{nd}$ office action, dated May 31, 2017, with an English Translation from Espacenet Global Dossier.

* cited by examiner

CORNEAL PRESERVATION AND REHYDRATION DEVICE

CROSS-REFERENCE TO RELATED APPLICATION

This is a national phase entry under 35 USC 371 of International Patent Application No. PCT/CN2016/092432 filed on Jul. 29, 2016, which application claims priority to Chinese Patent Application No. 201510466857.7 filed with the Chinese Patent Office on Jul. 31, 2015, titled "Corneal Preservation and Rehydration Device", and Chinese Utility Model Application No. 201520572717.3 filed with the Chinese Patent Office on Jul. 31, 2015, titled "Cornea Holding Device", the disclosures of which are incorporated herein by reference in their entireties.

TECHNICAL FIELD

The present disclosure relates to the technical field of corneal preservation, and in particular to a corneal preservation and rehydration device.

BACKGROUND

A cornea is one layer of a transparent film in the front part of an eye. When a cornea is damaged or has a lesion, a corneal transplantation surgery is in need for therapy. And a cornea used in the corneal transplantation surgery may be an artificial bio-cornea or a cornea donated from a human body.

The artificial bio-cornea or the cornea donated from a human body needs to be packaged, stored and transported prior to the transplantation surgery to avoid the cornea being contaminated or degenerating during its storage and transportation. During a procedure of corneal preservation, a cornea usually needs to be preserved or needs to be dried and preserved. A dried and preserved cornea, before use, needs to be placed in water for rehydration.

A packaging box in the prior art is a penicillin bottle or a common box body structure, and a cornea is placed directly in a box body for storage. In this way, the cornea is easy to slide off, overturn, get folds or deformation, or even be damaged during movement and transportation prior to clinical use, because the cornea is not positioned effectively in the packaging box. In a packaging box with desiccant to store, movement and sliding off of a cornea will cause the cornea to contact with the desiccant, and thus the cornea will be contaminated. Such that, it is not easy to maintain an original shape of a cornea, and it easily results in a change in obverse and reverse of an artificial bio-cornea, thus the clinical use will be affected. Furthermore, before the transplantation surgery is performed, a cornea usually needs to be rehydrated. A clinician needs to remove the cornea into another container to perform a rehydration procedure in the prior art, this undoubtedly increases the risk of contaminating and damaging the cornea.

SUMMARY

An embodiment of the present disclosure provides a corneal preservation and rehydration device, comprising a box body and a box lid, wherein the box body and the box lid are detachably connected. A corneal bracket is provided in the box body for holding a cornea, wherein a surface of the corneal bracket for placing a cornea is a convex spherical surface, and a blocking portion is provided at the surrounding of the convex spherical surface for preventing a cornea from dropping out.

BRIEF DESCRIPTION OF THE DRAWINGS

To describe the technical solutions in the embodiments of the present disclosure or in the prior art more clearly, the accompanying drawings to be used for describing the embodiments or the prior art will be introduced briefly. Obviously, the accompanying drawings to be described below are merely some of the embodiments of the present disclosure. And those skilled in the art can obtain other drawings according to these drawings without any creative effort.

DETAILED DESCRIPTION

The technical solutions in the embodiments of the present disclosure will be clearly and completely described below with reference to the accompanying drawings in the embodiments of the present disclosure. Apparently, the embodiments described herein are merely a part but not all of the embodiments of the present disclosure. All other embodiments obtained by those skilled in the art based on the embodiments of the present disclosure without any creative effort shall fall within the protection scope of the present disclosure.

In the description of the present disclosure, it shall be understood that the orientation or position relation indicated by terms "center", "upper", "lower", "front", "back", "left", "right", "vertical", "horizontal", "top", "bottom", "internal", "external" or the like is an direction or position relation shown based on the accompanying drawings merely for describing the present disclosure and simplifying the description, rather than indicating or implying that the indicated devices or components must have a particular orientation, or shall be constructed and operated in a particular orientation. Therefore the terms should not be interpreted as limitations to the present disclosure. Unless otherwise stated, in the description of the present disclosure, "a plurality of" means two or more.

An embodiment of the present disclosure provides a corneal preservation and rehydration device capable of effectively positioning, fixing and preserving a cornea and maintaining an original shape of the cornea so as to prevent the cornea from being deformed during movement and transportation.

Figure 1:
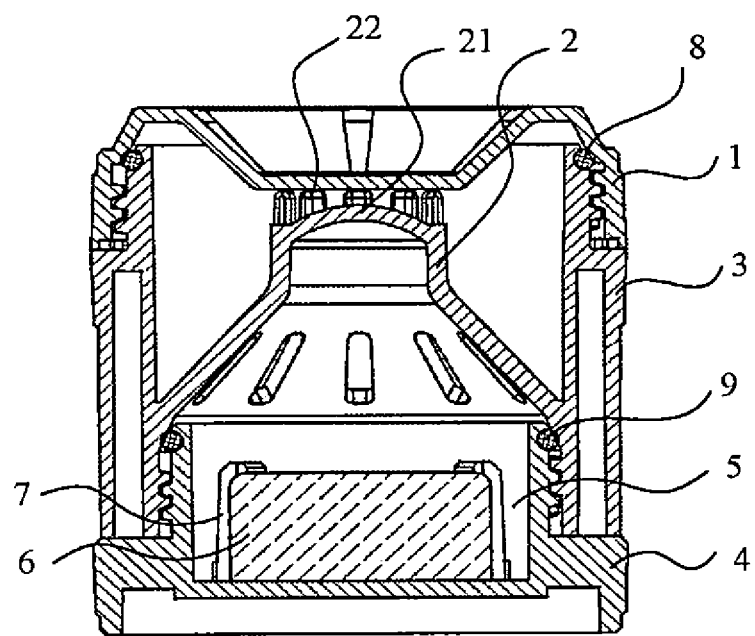
FIG. 1 is an assembly view of a corneal preservation and rehydration device according to an embodiment of the present disclosure.

Referring to FIG. 1, FIG. 1 shows a specific embodiment of a corneal preservation and rehydration device of the embodiments of the present disclosure. The corneal preservation and rehydration device of the embodiment includes a box body and a box lid 1, wherein the box body and the box lid 1 are detachably connected. A corneal bracket 2 is provided in the box body for holding a cornea, wherein a surface of the corneal bracket 2 for placing a cornea is a convex spherical surface 21, and a blocking portion 22 is provided at the surrounding of the convex spherical surface 21 for preventing a cornea from dropping out.

An embodiment of the present disclosure provides a corneal preservation and rehydration device. As the corneal bracket 2 is provided in the box body for holding a cornea, the cornea may be placed on the corneal bracket 2. As the surface of the corneal bracket 2 for placing a cornea is the convex spherical surface 21, and a cornea has a flake-shaped structure in a convex spherical type, a cornea may fit to the convex spherical surface 21 to maintain its original structure and shape. As the blocking portion 22 is provided at the surrounding of the convex spherical surface 21 to prevent a cornea from dropping out, the cornea may not slide off from the convex spherical surface 21. Before a cornea is used, water may be added into the box body to soak the cornea therein to rehydrate the cornea. Compared with the prior art, by using the above corneal preservation and rehydration device to pack a cornea, the cornea can be positioned effectively, fixed and preserved so as to avoid being deformed during movement and transportation. Also, before used, a cornea can be rehydrated inside this device, reducing the risk of contaminating the cornea through using anther container for hydration.

In the above embodiment, the connection way of the box body and the box lid 1 may be designed to be detachable connection to facilitate placement and removal of a cornea. And in order to realize the detachable connection of the box body and the box lid 1, the connecting portion of the box body and the box lid 1 can be made into a structure as shown in FIG. 1. Specifically, the external wall of the top part of the box body is provided with an external thread, and the side internal wall of the box lid 1 is provided with an internal thread which can match with this external thread. A threaded connection structure of the box body and the box lid 1 may make the procedure of removing and fitting the box lid 1 simple and smooth.

The box body may adopt a structure as shown in FIG. 1. Referring to FIG. 1, the box body includes a box trunk 3 and a box bottom 4 located under the bottom part of the box trunk 3. The corneal bracket 2 is located above the box bottom 4. A receiving cavity 5 is provided between the box bottom 4 and the corneal bracket 2. The box lid 1 is configured to cover the box body. A cornea-holding space is provided between the corneal bracket 2 and the box lid 1. The receiving cavity 5 and the cornea-holding space communicate. As a result, when a substance having a specific function is placed in the receiving cavity 5, a functioning space of the substance may extend to the cornea-holding space, so that a cornea placed in the cornea-holding space may be acted on.

In the above embodiment, in order to dry and preserve a cornea, desiccant having the function of drying a cornea may be placed in the receiving cavity 5. Referring to FIG. 1, desiccant 6 is placed in the receiving cavity 5. The desiccant 6 is able to absorb moisture from the corneal site, thereby achieving drying and preservation of a cornea.

Figure 2:
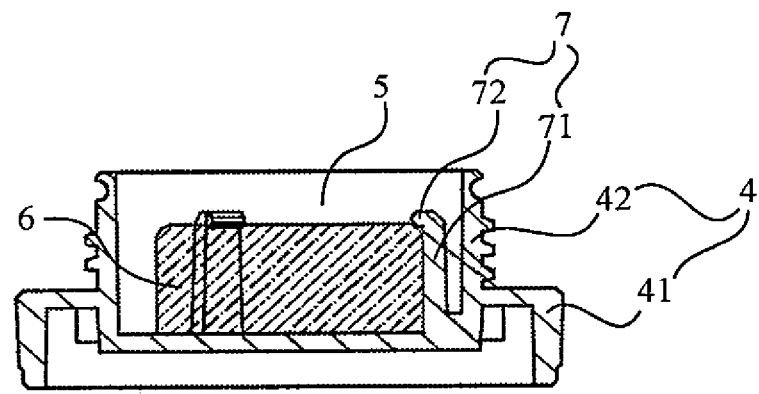
FIG. 2 is a cross-sectional view of a box bottom of a corneal preservation and rehydration device according to an embodiment of the present disclosure.

Further, in order to fix the desiccant 6 stored in the receiving cavity 5, the receiving cavity 5 is provided with a limiting structure 7 for fixing the desiccant 6. The limiting structure 7 may adopt a structure as shown in FIG. 2. Specifically, the limiting structure 7 consists of a plurality of fasteners with lower ends being connected to the bottom of the receiving cavity 5. The width of a gap between each adjacent two of the plurality of fasteners is less than a maximum width of the desiccant 6. Each of the plurality of fasteners includes a vertical protrusion 71 and a horizontal protrusion 72. The vertical protrusion 71 may be made into a cuboid structure as shown in FIG. 2, and also may be made into a cylindrical structure, and that is not limited herein. The horizontal protrusion 72 is arranged on the top of the vertical protrusion 71 and towards the central axis of the plurality of fasteners. Vertical protrusions 71 of the plurality of fasteners are used to prevent the desiccant 6 from moving horizontally, and horizontal protrusions 72 of the plurality of fasteners are used to prevent the desiccant 6 from moving up and down, so the position of the desiccant 6 is limited. A connection way of the box trunk 3 and the box bottom 4 may be designed to be detachable connection so as to facilitate the placement and removal of the desiccant.

Figure 3:
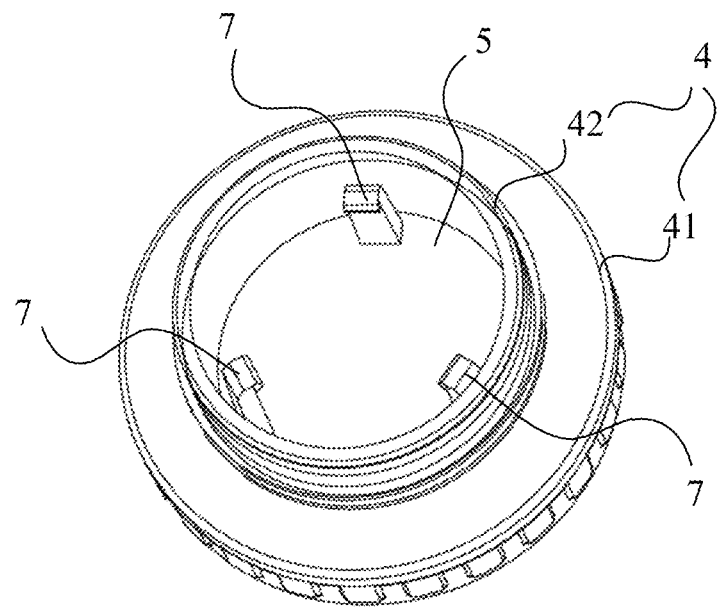
FIG. 3 is a perspective view of a box bottom of a corneal preservation and rehydration device according to an embodiment of the present disclosure.
Figure 7:
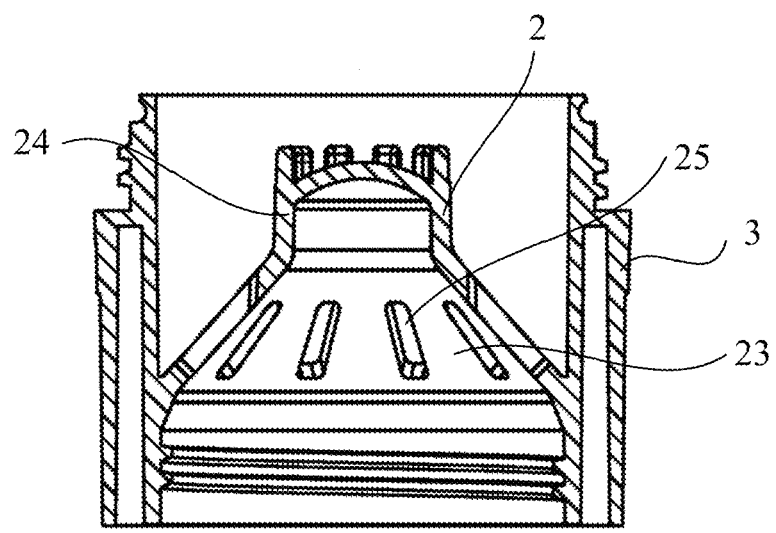
FIG. 7 is a cross-sectional view of a box trunk of a corneal preservation and rehydration device according to an embodiment of the present disclosure.

In order to realize the detachable connection of the box trunk 3 and the box bottom 4, the box bottom 4 preferably adopts a structure as shown in FIG. 3. Specifically, the box bottom 4 includes a base 41 and a tubular protrusion 42 which is arranged on the upper surface of the base. A cavity surrounded by the tubular protrusion 42 is the receiving cavity 5, the external wall of the tubular protrusion 42 is provided with an external thread. As shown in FIG. 7, the internal wall of the bottom part of the box trunk 3 is provided with an internal thread that may match with this external thread. A threaded connection structure of the box trunk 3 and the box bottom 4 may make the procedure of removing and fitting the box bottom 4 simple and smooth.

Figure 4:
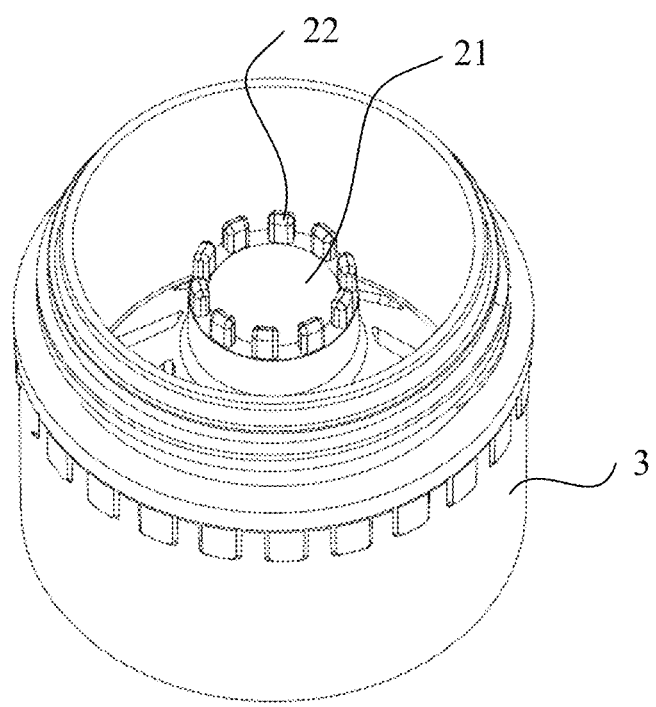
FIG. 4 is a perspective view of a box trunk of a corneal preservation and rehydration device according to an embodiment of the present disclosure.
Figure 5:
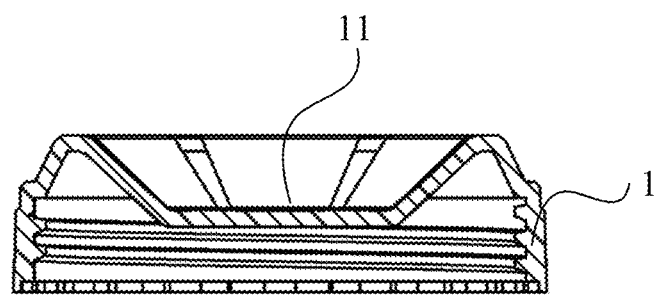
FIG. 5 is a cross-sectional view of a box lid of a corneal preservation and rehydration device according to an embodiment of the present disclosure.

Specifically, the blocking portion 22 may be a structure of a cylindrical tube with a lower end being connected to the edge of the convex spherical surface 21, and may also be a structure of a plurality of protruded poles arranged around the convex spherical surface 21. Compared with the above first solution, the above second solution may be used to effectively stop a cornea from slipping off from the convex spherical surface 21 and also facilitate placing and taking out a cornea via special tweezers, by reasonably designing a gap between each adjacent two of the plurality of protruded poles, and specifically, the width of this gap is made smaller than the maximum width of a cornea and larger than the width of the special tweezers for picking up a cornea. Therefore, it is preferable that the blocking portion 22 is the structure of a plurality of protruded poles arranged around the convex spherical surface 21 to effectively stop a cornea from slipping off from the convex spherical surface 21 and getting folds or deformation, and also to facilitate placing and taking out a cornea via special tweezers. And for example, the blocking portion 22 may be made as a structure as shown in FIG. 4. That is, the blocking portion 22 includes a plurality of protruded poles arranged around the convex spherical surface 21, there is a certain gap between each adjacent two of the plurality of protruded poles, and the width of the gap is 1~3 mm. Further, since a cornea may shake up and down during the movement and transportation, in addition to providing the blocking portion 22 in the corneal preservation and rehydration device to prevent a cornea from slipping off from the convex spherical surface 21, and a distance between the lower surface of the box lid 1 and the upper surface of the blocking portion 22 may also be reasonably arranged, to prevent a cornea from dropping out from a space between the lower surface of the box lid 1 and the upper surface of the blocking portion 22. Specifically, the distance between the upper surface of the blocking portion 22 and the lower surface of the box lid 1 is arranged to be less than 0.2 mm, to prevent a cornea from dropping out from the space between the lower surface of the box lid 1 and the upper surface of the blocking portion 22 due to that a cornea shakes upward and downward in a too large amplitude during the movement and transportation. In order to ensure avoiding that a cornea overturns in a space above the convex spherical surface and surrounded by the blocking portion so that the obverse and reverse of the cornea are shifted, the height of each of the plurality of protruded poles may be arranged to be smaller than the diameter of a cornea or even lower. In conclusion, a cornea is effectively prevented from overturning by height arrangement of the above protruded poles and distance arrangement between the blocking portion 22 and the box lid 1, thereby avoiding an influence on clinical use.

In order to ensure that the distance from the highest point of the blocking portion 22 to the lower surface of the box lid 1 is smaller, the blocking portion 22 may be designed to be higher so that the highest point of the blocking portion 22 is near the lower surface of the box lid 1, that is, the highest point of blocking portion 22 is higher than an upper end surface of the box body. Alternatively, the top external wall of the box lid 1 may be designed to be lower so that the lower surface of the box lid 1 approaches the highest point of the blocking portion 22, that is, the highest point of the blocking portion 22 is lower than the upper end surface of the box body. When the highest point of the blocking portion 22 is higher than the upper end surface of the box body, special tweezers may be poked into an area of the convex spherical surface 21 through one of side gaps of the blocking portion 22 to facilitate placing or taking out a cornea via special tweezers. In this case, rehydration operation may be as follows: pouring water into the box trunk 3, removing a cornea from the convex spherical surface 21 via special tweezers, putting the cornea into the water within the box trunk 3 for rehydration, removing the cornea after a period of time, and then the corneal rehydration operation being completed. When the highest point of the blocking portion 22 is lower than the upper end surface of the box body, in the case that a cornea needs to be preserved by a preservation solution, the preservation solution in the box trunk may reach a level of the position that a cornea can be completely submerged so as to preserve a cornea effectively. In addition, since the highest point of the blocking portion 22 is lower than the upper end surface of the box body, specific processes of the rehydration operation may be simplified as follows: directly pouring water into the box trunk to make a cornea be soaked in the water, and removing the cornea after a period of time, and then the rehydration of the cornea being completed. The operation is simple and convenient. Preferably, the water used for rehydration is water adequate for clinical use, preferably water for injection.

The highest point of the blocking portion 22 is the highest point of the plurality of protruded poles. Specifically, when the heights of the plurality of protruded poles are the same, the highest point of the blocking portion 22 is a top position of any one of the plurality of protruded poles; when the heights of the plurality of protruded poles are different, the highest point of the blocking portion 22 is the top position of the highest one of the plurality of protruded poles.

Figure 6:
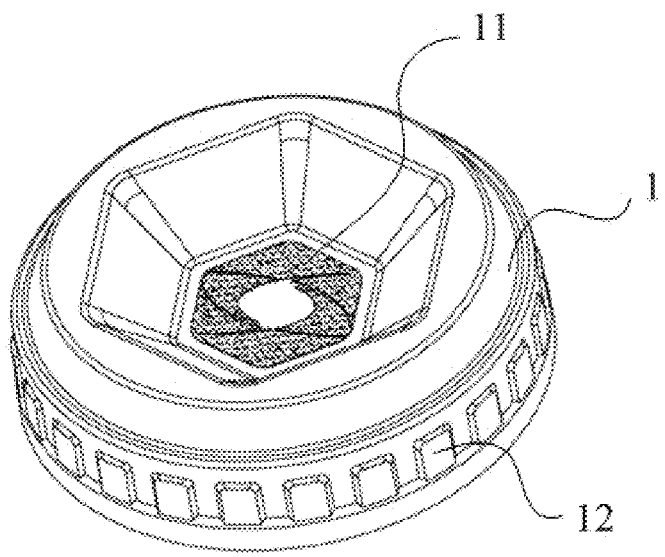
FIG. 6 is a perspective view of a box lid of the corneal preservation and rehydration device according to an embodiment of the present disclosure.

When the top external wall of the box lid 1 is recessed towards the blocking portion 22, a recessed portion 11 may adopt a structure as shown in FIG. 6, that is, the shape of the recessed portion 11 is a regular hexagon. Of course, the shape of the recessed portion 11 may also be a circle, oval or triangle, etc. And the position of the recessed portion 11 may be at a central position of the box lid 1 or also may not be at the central position of the box lid 1, and that is not limited herein.

Specifically, the corneal bracket 2 may adopt a structure as shown in FIG. 7. The corneal bracket 2 includes a supporting plate 23 and a boss 24 arranged on the supporting plate. The boss 24 protrudes in a direction approaching the box lid 1. The upper surface of the boss 24 is the convex spherical surface 21 for placing a cornea. The supporting plate 23 is used to support the boss 24 arranged thereon. The edge of the supporting plate 23 is connected to the internal wall of the box trunk 3. The supporting plate 23 is provided with through holes 25 penetrating both upper and lower surfaces of the supporting plate 23. The through holes 25 connect two cavities of the upper and the lower separated by the supporting plate 23, wherein a cavity below the supporting plate 23 is the receiving cavity 5, and a cavity above the supporting plate 23 is the cornea-holding space for placing a cornea.

Connection of the supporting plate 23 and the box trunk 3 may be made as detachable connection, and it is also possible to make the supporting plate 23 and the box trunk 3 as an integrated molded structure. When the first solution is adopted, the supporting plate 23 and the box trunk 3 are two different components, which need to be separately manufactured, so a manufacturing process is complicated. Therefore, in order to avoid the above-mentioned problems, it is preferable that the supporting plate 23 and the box trunk 3 are made as the integrated molded structure, and for example, may be made as a structure shown in FIG. 7, thereby simplifying the manufacturing process.

In addition, the boss 24 may be in a cylindrical type or a cuboid type. Of course, the boss 24 may also be in other shapes. And that is not limited herein.

Further, since the supporting plate 23 is used to support the boss 24 provided thereon, the supporting plate 23 subjects to pressure from the boss 24. In order to prevent the supporting plate 23 from being deformed due to the pressure, the structure of the supporting plate 23 needs to be reasonably designed. The supporting plate 23 may adopt a conical plate structure, and may also adopt a flat plate structure. The conical plate structure is less susceptible to deformation than the plate structure when the supporting plate 23 subjects to a constant pressure from the boss, therefore, the supporting plate 23 is preferably made as the conical plate structure, and for example, made as the conical plate structure as shown in FIG. 7.

In order to enable the desiccant stored in the receiving cavity 5 to uniformly and effectively dry a cornea, the through holes 25 are preferably uniformly arranged on the conical plate, and the shape of each of the through holes 25 may be rectangular, circular, polygonal, etc., which is not limited herein.

In order to preserve a cornea at a constant temperature, a thermal insulation structure may be provided in the corneal preservation and rehydration device. In the embodiment shown in FIG. 1, the side wall of the box body may be made in a structure of two layers. There is a gap between an internal layer and an external layer of the side wall of the box body, and this gap is filled with air. Since air is poor conductor of heat, heat exchange between the inside and the outside of the corneal preservation and rehydration device may be hindered, thereby achieving preserving a cornea at a constant temperature.

Referring to FIG. 1, the box body has a side wall with a structure of two layers, and the gap between the two layers of the side wall is filled with air. In order to increase the strength of the side wall of the box body, a stiffening rib may be arranged in this gap of the structure of two layers to prevent the box body from being deformed due to squeezing from the outside world.

In order to ensure good leakproofness of the corneal preservation and rehydration device, a first sealing ring 8 may be arranged at a connecting position of the box trunk 3 and the box lid 1, and a second sealing ring 9 is arranged at a connecting position of the box bottom 4 and the box trunk 3. Specifically, along one perimeter of the external wall of the box trunk 3, a groove for placing the first seal ring 8 may be arranged with a depth smaller than the diameter of the first sealing ring 8, and then, the first seal ring 8 is arranged therein. Along one perimeter of the external wall of the tubular protrusion 42, a groove for placing the second seal ring 9 may be arranged with a depth smaller than the diameter of the second sealing ring 9, and then, the second sealing ring 9 is arranged therein. Therefore, after the box trunk 3 and the box lid 1 are connected, a portion of the first sealing ring 8 located outside the corresponding groove may be pressed by the side internal wall of the box lid 1 to achieve a sealed connection of the box trunk 3 and the box lid 1. Similarly, after the box bottom 4 and the box trunk 3 are connected, a portion of the second sealing ring 9 located outside the corresponding groove may be pressed by the internal side wall of the box trunk 3 to achieve a sealed connection of the box bottom 4 and the box trunk 3. As a result, overall leakproofness of the corneal preservation and rehydration device may be ensured, thereby preventing external air and impurities from entering the corneal preservation and rehydration device and affecting a cornea. In addition, when there is preservation solution stored inside the corneal preservation and rehydration device, the preservation solution may be prevented from flowing out.

In order to maintain the structure and shape of a cornea more effectively, it is preferable that the curvature of the convex spherical surface 21 is similar to the curvature of a cornea, so that a cornea may completely fit to the convex spherical surface 21, thereby effectively preventing deformation of a cornea.

Figure 8:
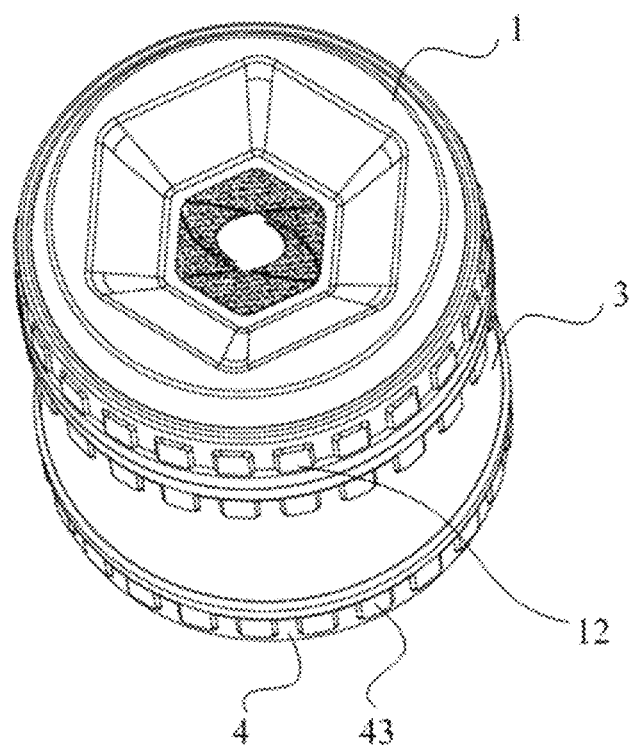
FIG. 8 is a perspective view of a corneal preservation and rehydration device according to an embodiment of the present disclosure.

Because the connection of the box trunk 3 and the box lid 1 as well as that of the box trunk 3 and the box bottom 4 are both threaded connections, the components need to be rotated during disassembly and installation. In order to prevent a slip phenomenon during a rotating process, referring to FIG. 8, it is preferable to provide first anti-slip protrusions 12 and second anti-slip protrusions 43 on the side external wall of the box lid 1 and the external wall of the box bottom 4, respectively, so as to facilitate disassembly and installation of the box trunk 3 and the box lid 1, as well as those of the box trunk 3 and the box bottom 4.

The foregoing descriptions merely show specific implementations of the present disclosure, and the protection scope of the present disclosure is not limited thereto. Any skilled in the art can readily conceive of variations or replacements within the technical scope disclosed by the present disclosure, and these variations or replacements shall fall into the protection scope of the present disclosure. Therefore, the protection scope of the present disclosure should be subject to the protection scope of the claims.

What is claimed is:

1. A corneal preservation and rehydration device, comprising a box body and a box lid, wherein the box body and the box lid are detachably connected, and a corneal bracket is provided in the box body for holding a cornea, wherein a surface of the corneal bracket for placing a cornea is a convex spherical surface, and a blocking portion is provided at the surrounding of the convex spherical surface for preventing a cornea from dropping out; wherein
  the box body comprises a box trunk and a box bottom which is located under a bottom part of the box trunk; the corneal bracket is located above the box bottom; a receiving cavity is provided between the box bottom and the corneal bracket; the box lid is configured to cover the box body; a cornea-holding space is provided between the corneal bracket and the box lid; and, the receiving cavity and the cornea-holding space communicate; and
  a limiting structure is provided in the receiving cavity for fixing desiccant; and, the box trunk and the box bottom are detachably connected; and
  the box bottom comprises a base and a tubular protrusion which is arranged on an upper surface of the base; a cavity surrounded by the tubular protrusion is the receiving cavity; and an external wall of the tubular protrusion is provided with an external thread, matching with an internal thread which is provided in an internal wall of the bottom part of the box trunk.

2. The corneal preservation and rehydration device according to claim 1, wherein the blocking portion comprises a plurality of protruded poles arranged along the circumference of the convex spherical surface, there is a gap between each adjacent two of the plurality of protruded poles, and the width of the gap is 1-3 mm.

3. The corneal preservation and rehydration device according to claim 1, wherein a distance between a highest point of the blocking portion and a lower surface of the box lid is less than 0.2 mm.

4. The corneal preservation and rehydration device according to claim 1, wherein an upper end surface of the box body is higher than the highest point of the blocking portion, and a top external wall of the box lid is recessed in a direction approaching the blocking portion.

5. The corneal preservation and rehydration device according to claim 1, wherein the corneal bracket comprises a supporting plate and a boss arranged on the supporting plate, the boss protrudes in a direction approaching the box lid, an upper surface of the boss is the convex spherical surface of the corneal bracket for placing a cornea, an edge of the supporting plate is connected to the internal wall of the box trunk, and the supporting plate is provided with through holes penetrating the supporting plate.

6. The corneal preservation and rehydration device according to claim 5, wherein the supporting plate is a conical plate, and the through holes are uniformly arranged on the conical plate.

7. The corneal preservation and rehydration device according to claim 1, wherein the box body has a side wall of two layers including the internal wall, and there is a gap between the two layers, with a stiffening rib provided therein.

8. The corneal preservation and rehydration device according to claim 1, wherein a top part of the box trunk is provided with an external thread, matching with an internal thread which is provided in a side internal wall of the box lid; a first sealing ring is arranged on a connecting position of the box trunk and the box lid; and a second sealing ring is arranged on a connecting position of the box trunk and the box bottom.

9. The corneal preservation and rehydration device according to claim 1, wherein the curvature of the convex spherical surface is similar to the curvature of a cornea.

\* \* \* \* \*

UNITED STATES PATENT AND TRADEMARK OFFICE
CERTIFICATE OF CORRECTION

PATENT NO. : 10,952,429 B2
APPLICATION NO. : 15/745123
DATED : March 23, 2021
INVENTOR(S) : Jinnan Zhang et al.

Page 1 of 1

It is certified that error appears in the above-identified patent and that said Letters Patent is hereby corrected as shown below:

On the Title Page

Item (30) Foreign Application Priority Data:
"Jul. 31, 2015 (CN) ................................ 201510466857.7"

Is changed to:
-- Jul. 31, 2015 (CN) ................................ 201510466857.7
Jul. 31, 2015 (CN) ................................ 201520572717.3 --

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*